United States Patent
Wells et al.

(10) Patent No.: US 6,930,078 B2
(45) Date of Patent: Aug. 16, 2005

(54) SHAMPOO CONTAINING A CATIONIC GUAR DERIVATIVE

(75) Inventors: Robert Lee Wells, Cincinnati, OH (US); Eric Scott Johnson, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 147 days.

(21) Appl. No.: 10/420,220

(22) Filed: Apr. 22, 2003

(65) Prior Publication Data

US 2003/0199403 A1 Oct. 23, 2003

Related U.S. Application Data

(60) Provisional application No. 60/374,602, filed on Apr. 22, 2002.

(51) Int. Cl.$^7$ .................................................. C11D 3/22
(52) U.S. Cl. ..................... 510/121; 510/119; 510/122; 510/466; 510/504; 424/70.11; 424/70.12; 424/70.28
(58) Field of Search ................................ 510/119, 121, 510/122, 466, 504; 424/70.11, 70.12, 70.28

(56) References Cited

U.S. PATENT DOCUMENTS

| | | | | |
|---|---|---|---|---|
| 4,292,212 | A | * 9/1981 | Melby ........................ | 510/121 |
| 4,943,430 | A | 7/1990 | Hefford et al. | |
| 5,186,928 | A | * 2/1993 | Birtwistle ................... | 424/70.9 |
| 5,372,804 | A | * 12/1994 | Khoshdel et al. ............ | 424/59 |
| 5,624,666 | A | * 4/1997 | Coffindaffer et al. ..... | 424/70.21 |
| 5,632,998 | A | 5/1997 | Midha et al. | |
| 5,662,892 | A | 9/1997 | Bolich, Jr. | |
| 5,710,113 | A | 1/1998 | Wells | |
| 5,720,964 | A | * 2/1998 | Murray ....................... | 424/401 |
| 5,723,112 | A | 3/1998 | Bowser et al. | |
| 5,756,436 | A | 5/1998 | Royce et al. | |
| 5,776,871 | A | * 7/1998 | Cothran et al. ............. | 510/122 |
| 5,811,087 | A | 9/1998 | Mohring et al. | |
| 5,843,875 | A | 12/1998 | Wei et al. | |
| 5,874,073 | A | 2/1999 | Kaiser et al. | |
| 5,876,705 | A | 3/1999 | Uchiyama et al. | |
| 5,932,202 | A | 8/1999 | Guskey et al. | |
| 5,932,203 | A | * 8/1999 | Coffindaffer et al. ..... | 424/70.19 |
| 5,977,038 | A | * 11/1999 | Birtwistle et al. .......... | 510/122 |
| 5,980,877 | A | * 11/1999 | Baravetto et al. ......... | 424/70.12 |
| 5,990,059 | A | * 11/1999 | Finel et al. .................. | 510/122 |
| 6,040,282 | A | * 3/2000 | Guskey et al. .............. | 510/119 |
| 6,297,203 | B1 | 10/2001 | Guskey | |
| 6,335,312 | B1 | * 1/2002 | Coffindaffer et al. ....... | 510/159 |
| 6,451,300 | B1 | * 9/2002 | Dunlop et al. ........... | 424/70.27 |
| 6,511,669 | B1 | 1/2003 | Garnier et al. | |

FOREIGN PATENT DOCUMENTS

| | | |
|---|---|---|
| EP | 0093601 A2 | 11/1983 |
| FR | 2773990 A1 | 7/1999 |
| WO | WO-93/08787 A2 | 5/1993 |
| WO | WO-94/06403 A1 | 3/1994 |
| WO | WO-94/06409 A1 | 3/1994 |
| WO | WO-97/29736 A1 | 1/1997 |
| WO | WO-97/35549 A1 | 10/1997 |
| WO | WO-99/39683 A1 | 8/1999 |
| WO | WO-00/66072 A1 | 11/2000 |
| WO | WO-00/66081 A1 | 11/2000 |
| WO | WO-01/97761 A1 | 12/2001 |

OTHER PUBLICATIONS

Hossel, P. et al., "Conditioning Polymers in today's shampoo formulations—efficacy, mechanism, and test methods", *International Journal of Cosmetic Science*, 2000, pp. 1–10, vol. 22, No. 1, BASF, Ludwigshafen Germany, XP002250154.

* cited by examiner

*Primary Examiner*—Charles Boyer
(74) *Attorney, Agent, or Firm*—Marianne Dressman; Tara M. Rosnell

(57) ABSTRACT

The compositions of the present invention relate to improved shampoo compositions having from about from about 5 to about 50 weight percent of a detersive surfactant, at least about 0.05 weight percent of a cationic polymer least about 0.05 weight percent of a cationic guar derivative having a molecular weight from about 10,000 to about 10,000,000 and a charge density from about 1.25 meq/g to about 7 meq/g, and at least about 20.0 weight percent of an aqueous carrier.

8 Claims, No Drawings

SHAMPOO CONTAINING A CATIONIC GUAR DERIVATIVE

CROSS REFERENCE TO RELATED APPLICATION

The application claims the benefit of U.S. Provisional application Ser. No. 60/374,602, filed on Apr. 22, 2002.

FIELD

The present invention relates to a hair cleansing shampoo containing a cationic guar derivative. More specifically, it relates to a shampoo containing a cationic guar derivative having a high charge density.

BACKGROUND

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. Shampooing can also result in the hair becoming dry or "frizzy", and a loss of luster, due to removal of natural oils or other hair moisturizing materials. After shampooing, the hair can also suffer from a loss of "softness" perceived by the user upon drying. The hair can also suffer from increased levels of static upon drying after shampooing. This can interfere with combing and can result in fly-away hair. A variety of approaches have been developed to alleviate the after-shampoo problems. These range from the inclusion of hair conditioning aids in shampoos to post-shampoo application of hair conditioners, i.e., hair rinses. Hair rinses are generally liquid in nature and must be applied in a separate step following the shampooing, left on the hair for a length of time, and rinsed with fresh water. This, of course, is time consuming and is not as convenient as shampoos containing both cleaning and hair conditioning ingredients. Therefore, it is desirable to have a shampoo capable of depositing conditioning aids.

It is also desirable to include solid particles in a shampoo for deposition on the scalp and/or hair. Solid particles are known for use as benefit agents in a variety of formulations and personal care compositions. Solid particles can impart benefits both to the compositions comprising them or surfaces to which the compositions are applied. Solid particles can for example be used as pigments or coloring agents, opacifiers, pearlescent agents, feel modifiers, oil absorbers, skin protectants, matting agents, friction enhancers, slip agents, conditioning agents, exfoliants, odor absorbers, or cleaning enhancers. Additionally, many active ingredients useful as treatment agents for various disorders or socially embarrassing conditions are available and typically used in solid particulate form including antiperspirant agents, antidandruff agents, antimicrobials, antibiotics, and sunscreens.

Depositing materials such as conditioning aids and solid particles from a shampoo composition can be difficult. Deposition must be balanced against other factors such as cleansing properties of the shampoo, "feel" of the shampoo during use, and hair feel post-shampoo. Current polymers used as deposition aids are not always effective at depositing materials while maintaining the balance described above.

It remains, therefore, highly desirable to have a rinse-off composition, preferably a cleansing composition, capable of containing and effectively depositing and retaining conditioning aids and/or solid particle benefit agents on the surface treated therewith. It has now been discovered that select cationic polymers, when used in the cleansing compositions of the present invention, can surprisingly enhance the deposition and retention of conditioning aids and/or solid particle benefit agents on the surfaces treated therewith.

SUMMARY

The present invention is directed to a shampoo composition comprising:
   a) from about 5 to about 50 weight percent of a detersive surfactant,
   b) at least about 0.05 weight percent of a cationic guar derivative;
      i) wherein said cationic guar derivative has a molecular weight from about 10,000 to about 10,000,000; and
      ii) wherein said cationic guar derivative has a charge density from about 1.25 meq/g to about 7 meq/g; and
   c) at least about 20.0 weight percent of an aqueous carrier.

The present invention is further directed to a method of using the shampoo composition.

These and other features, aspects, and advantages of the present invention will become evident to those skilled in the art from a reading of the present disclosure.

DETAILED DESCRIPTION

While the specification concludes with claims which particularly point out and distinctly claim the invention, it is believed the present invention will be better understood from the following description.

The shampoo compositions of the present invention include detersive surfactant, a cationic guar derivative and an aqueous carrier. Each of these essential components, as well as preferred or optional components, are described in detail hereinafter.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified.

All molecular weights as used herein are weight average molecular weights expressed as grams/mole, unless otherwise specified.

The term "charge density", as used herein, refers to the ratio of the number of positive charges on a monomeric unit of which a polymer is comprised to the molecular weight of said monomeric unit. The charge density multiplied by the polymer molecular weight determines the number of positively charged sites on a given polymer chain.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "fluid" as used herein, means a liquid or a gas which tends to take the shape of its container, container being the wall of the flexible hollow particles.

The term "flexible" as used herein, means that the hollow particles of the present invention are easy to compress but when pressure is reduced the hollow particles regain their original volume.

The term "fluid-encapsulated" as used herein, means that the hollow particles of the invention are structurally hollow. In accordance with the invention, the term "structurally hollow" nonetheless allows the hollow particles to contain at least one additional material therein.

The term "hollow" as used herein, means a particle having an encapsulated area that is substantially free of solid mass, the encapsulated area comprising from 10 to 99.8 percent of the total volume of the particle.

The term "permeable" as used herein, means that a substance that permits a liquid or gas to pass through it under given conditions.

The term "polymer" as used herein shall include materials whether made by polymerization of one type of monomer or made by two (i.e., copolymers) or more types of monomers.

The term "solid particle" as used herein means a particle that is not a liquid or a gas.

The term "sphere" as used herein, means a spherical body which is the set of points in a metric space whose distance from a fixed point is approximately constant. Here, the meaning of "approximately" is that the fixed points are within a distance of ±15%.

The term "suitable for application to human hair" as used herein, means that the compositions or components thereof so described are suitable for use in contact with human hair and the scalp and skin without undue toxicity, incompatibility, instability, allergic response, and the like.

The term "water soluble" as used herein, means that the polymer is soluble in water in the present composition. In general, the polymer should be soluble at 25° C. at a concentration of 0.1% by weight of the water solvent, preferably at 1%, more preferably at 5%, most preferably at 15%.

All cited references are incorporated herein by reference in their entireties. Citation of any reference is not an admission regarding any determination as to its availability as prior art to the claimed invention.

A. Detersive Surfactant

The shampoo composition of the present invention includes a detersive surfactant. The detersive surfactant component is included to provide cleaning performance to the composition. The detersive surfactant component in turn comprises anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the shampoo composition herein include those which are known for use in hair care or other personal care cleansing compositions. The concentration of the anionic surfactant component in the shampoo composition should be sufficient to provide the desired cleaning and lather performance, and generally range from about 5% to about 50%, preferably from about 8% to about 30%, more preferably from about 10% to about 25%, even more preferably from about 12% to about 22%, by weight of the composition.

Preferred anionic surfactants suitable for use in the shampoo compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Solubility of the surfactant will depend upon the particular anionic detersive surfactants and cations chosen.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Specific non limiting examples of alkyl ether sulfates which may be used in the shampoo compositions of the present invention include sodium and ammonium salts of coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide.

Other suitable anionic detersive surfactants are the water-soluble salts of organic, sulfuric acid reaction products conforming to the formula $[R^1—SO_3—M]$ where $R^1$ is a straight or branched chain, saturated, aliphatic hydrocarbon radical having from about 8 to about 24, preferably about 10 to about 18, carbon atoms; and M is a cation described hereinbefore. Non limiting examples of such detersive surfactants are the salts of an organic sulfuric acid reaction product of a hydrocarbon of the methane series, including iso-, neo-, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486, 922; and 2,396,278, which descriptions are incorporated herein by reference.

Other anionic detersive surfactants suitable for use in the shampoo compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxyalkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms, preferably from about 12 to about 16 carbon atoms. Preferably, they are straight chain olefins. In addition to the true alkene sulfonates and a proportion of hydroxyalkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880, which description is incorporated herein by reference.

Another class of anionic detersive surfactants suitable for use in the shampoo compositions are the beta-alkyloxy alkane sulfonates. These surfactants conform to the formula

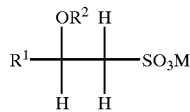

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic detersive surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Suitable amphoteric or zwitterionic detersive surfactants for use in the shampoo composition herein include those which are known for use in hair care or other personal care cleansing. Concentration of such amphoteric detersive surfactants preferably ranges from about 0.5% to about 20%, preferably from about 1% to about 10%, by weight of the composition. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.), which descriptions are incorporated herein by reference.

Amphoteric detersive surfactants suitable for use in the shampoo composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the shampoo composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The shampoo compositions of the present invention may further comprise additional surfactants for use in combination with the anionic detersive surfactant component described hereinbefore. Suitable optional surfactants include nonionic surfactants. Any such surfactant known in the art for use in hair or personal care products may be used, provided that the optional additional surfactant is also chemically and physically compatible with the essential components of the shampoo composition, or does not otherwise unduly impair product performance, aesthetics or stability. The concentration of the optional additional surfactants in the shampoo composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the shampoo compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which descriptions are incorporated herein by reference.

B. Cationic Guar Derivative

The composition of the present invention includes a cationic guar derivative of sufficiently high cationic charge density to effectively enhance deposition of conditioning aids and.or solid particles. Suitable cationic guar derivatives will have cationic charge densities of at least about 1.25 meq/gm, preferably at least about 1.5 meq/gm, more preferably at least about 1.7 meq/gm, even more preferably at least about 1.8 meq/gm, still more preferably at least about 2.0 meq/gm, and even more preferably at least about 2.3 meq/gm, but also preferably less than about 7 meq/gm, more preferably less than about 5 meq/gm, still more preferably less than about 4.5 meq/gm, at the pH of intended use of the shampoo composition, which pH will generally range from about pH 3 to about pH 9, preferably between about pH 4 and about pH 8. The average molecular weight of such suitable cationic guar derivatives will generally be between about 10,000 and 10 million, preferably between about 50,000 and about 5 million, more preferably between about 100,000 and about 3 million. The "cationic charge density" of a cationic guar derivative, as that term is used herein, refers to the ratio of the number of positive charges on a monomeric unit of which the polymer is comprised to the molecular weight of said monomeric unit. The cationic charge density multiplied by the polymer molecular weight determines the number of positively charged sites on a given polymer chain.

The concentration of the cationic guar derivative in the shampoo composition ranges from about 0.05% to about 3%, preferably from about 0.075% to about 2.0%, more preferably from about 0.1% to about 1.0%, by weight of the shampoo composition. The weight ratio of cationic derivative to particle (when this optional component is used) in the shampoo compositions is from about 2:1 to about 1:30, preferably from about 1:1 to about 1:20, more preferably from about 1:2 to about 1:10.

1. Characteristics of the Cationic Guars

The cationic guars useful in the present invention must be selected and must be present at a level such that the cationic polymers are soluble in the shampoo composition, and which are preferably soluble in a complex coacervate phase in the shampoo composition, upon dilution. Such coacervate is described in detail below. Also, physical properties of the cationic guars and suitable counterions are detailed.

i. Coacervate Formed from Cationic Polymer

A coacervate is formed, upon dilution of the shampoo composition, between the cationic polymer and the detersive surfactant component (described above) of the present invention. Coacervate formation is dependent upon a variety of criteria, such as molecular weight, component concentration, and ratio of interacting ionic components, ionic strength (including modification of ionic strength, for example, by addition of salts), charge density of the cationic and anionic components, pH, and temperature. Coacervate systems and the effect of these parameters have been described, for example, in J. Caelles, et al., "Anionic and Cationic Compounds in Mixed Systems", *Cosmetics & Toiletries*, vol. 106, (April 1991), pp 49–54; C. J. van Oss, "Coacervation, Complex-Coacervation and Flocculation", *J. Dispersion Science and Tech.*, vol. 9 (5,6), (1988–89), pp 561–73; and in D. J. Burgess, "Practical Analysis of Complex Coacervate Systems", *J. of Colloid and Interface Science*, vol. 140, no. 1, (November 1990), pp 227–38; all of which descriptions are incorporated herein by reference. The shampoo compositions described herein, typically have a ratio of anionic detersive surfactant component to cationic polymer component from about 25:0.02 to about 1:1, preferably from about 20:0.1 to about 12:1.

Coacervates are believed to provide conditioning benefits, especially conditioning benefits during product use when the hair is wet, by helping to deposit conditioning agents on the hair and scalp. Coacervates are also known in the art to aid deposition of other types of particulates. This is thought to occur by concentrating particulates within coacervate boundaries upon dilution.

Techniques for analysis of formation of complex coacervates are known in the art. For example, microscopic analyses of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the shampoo composition.

ii. Counterions Used in Forming Cationic Guars

Any anionic counterions may be use in association with the cationic guars so long as the cationic guars remain soluble in water, in the shampoo composition, or in a coacervate phase of the shampoo composition, and so long as the counterions are physically and chemically compatible with the essential components of the shampoo composition or do not otherwise unduly impair product performance, stability or aesthetics. Non-limiting examples of such counterions include: halides (e.g., chloride, fluoride, bromide, iodide), sulfate, methylsulfate, and mixtures thereof.

2. Chemical Description of the Cationic Guar Derivatives

Guars are cationically substituted galactomannan (guar) gum derivatives. Guar gum for use in preparing these guar gum derivatives is typically obtained as a naturally occurring material from the seeds of the guar plant. The guar molecule itself is a straight chain mannan branched at regular intervals with single membered galactose units on alternative mannose units. The mannose units are linked to each other by means of β (1–4) glycosidic linkages. The galactose branching arises by way of an α (1–6) linkage. Cationic derivatives of the guar gums are obtained by reaction between the hydroxyl groups of the polygalactomannan and reactive quaternary ammonium compounds. The degree of substitution of the cationic groups onto the guar structure must be sufficient to provide the requisite cationic charge density described above.

Suitable quaternary ammonium compounds for use in forming the cationic guar polymers include those conforming to the general Formula (XII):

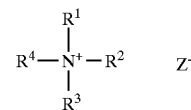

wherein where $R^1$, $R^2$ and $R^3$ are methyl or ethyl groups; $R^4$ is either an epoxyalkyl group of the general Formula (XIII):

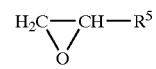

or $R^4$ is a halohydrin group of the general Formula (XIV):

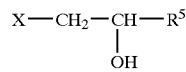

wherein $R^5$ is a $C_1$ to $C_3$ alkylene; X is chlorine or bromine, and Z is an anion such as $Cl^-$, $Br^-$, $I^-$ or $HSO_4^-$.

Cationic guar polymers (cationic derivatives of guar gum) formed from the reagents described above are represented by the general Formula (XV):

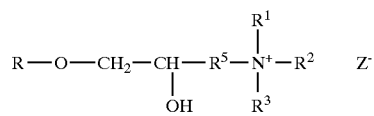

wherein R is guar gum. Preferably, the cationic guar polymer is guar hydroxypropyltrimethylammonium chloride, which can be more specifically represented by the general Formula (XVI):

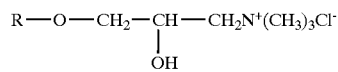

C. Aqueous Carrier

The compositions of the present invention include an aqueous carrier. The level and species of the carrier are selected according to the compatibility with other components, and other desired characteristic of the product.

Carriers useful in the present invention include water and water solutions of lower alkyl alcohols. Lower alkyl alcohols useful herein are monohydric alcohols having 1 to 6 carbons, more preferably ethanol and isopropanol.

Preferably, the aqueous carrier is substantially water. Deionized water is preferably used. Water from natural sources containing mineral cations can also be used, depending on the desired characteristic of the product. Generally, the compositions of the present invention comprise from about 20% to about 99%, preferably from about 40% to about 98%, and more preferably from about 60% to about 98% aqueous carrier.

The pH of the present composition is preferably from about 4 to about 9, more preferably from about 4.5 to about 7.5. Buffers and other pH adjusting agents can be included to achieve the desirable pH.

D. Additional Components

The shampoo compositions of the present invention may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10% by weight of the shampoo compositions.

Non-limiting examples of optional components for use in the shampoo composition include particles, cationic polymers, conditioning agents (hydrocarbon oils, fatty esters, silicones), anti dandruff agents, suspending agents, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

Particles

The composition of the present invention optionally includes particles. The particles of the present invention preferably have a particle size of less than 300 μm. Typically, the particles will have a particle size from about 0.01 μm to about 80 μm, still more preferably from about 0.1 μm to about 70 μm, and even more preferably from about 1 μm to about 60 μm in diameter.

Typical particle levels are selected for the particular purpose of the composition. As example, where it is desired to deliver color benefits, pigment particles confering the desired hues can be incorporated. Where hair volume or style retention benefits are desired, particles capable of conferring friction can be used to reduce disruption and collapse of the hair style. Where conditioning or slip is desired, suitable platelet or spherical particles can be incorporated. Determination of the levels and particle types is within the skill of the artisan. Particles that are generally recognized as safe, and are listed in C.T.F.A. Cosmetic Ingredient Handbook, Sixth Ed., Cosmetic and Fragrance Assn., Inc., Washington D.C. (1995), incorporated herein by reference, can be used.

In the compositions of the present invention, it is preferable to incorporate at least 0.025% by weight of particles, more preferably at least 0.1%, still more preferably at least 0.2%, and even more preferably at least 0.5% by weight of particles. In the compositions of the present invention, it is preferable to incorporate no more than about 20% by weight of particles, more preferably no more than about 10%, still more preferably no more than 5%, and even more preferably no more than 2% by weight of particles.

The particle may be colored or non-colored (for example white). Suitable powders include bismuth oxychloride, titanated mica, fumed silica, spherical silica, polymethylmethacrylate, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystaline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature.

The powder component may also comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarine and chromium or chromium hydroxide colors, and mixtures thereof.

Water insoluble solid particles of various shapes and densities are useful. In a preferred embodiment, the particles tend to have a spherical, an oval, an irregular, or any other shape in which the ratio of the largest dimension to the smallest dimension (defined as the aspect ratio) is less than 10. More preferably, the aspect ratio of the particles is less than 8. Still more preferably, the aspect ratio of the particles is less than 5.

Particles useful in the present invention can be natural, synthetic, or semi-synthetic in composition. Hybrid particles are also useful. Synthetic particles can made of either cross-linked or non cross-linked polymers. The particles of the present invention can have surface charges or their surface can be modified with organic or inorganic materials such as surfactants, polymers, and inorganic materials. Particle complexes are also useful.

Non limiting examples of natural particles include various precipitated silica particles in hydrophilic and hydrophobic forms available from Degussa-Huls under the trade name Sipernet. Snowtex colloidal silica particles available from Nissan Chemical America Corporation.

Examples of synthetic particles include nylon, silicone resins, poly(meth)acrylates, polyethylene, polyester, polypropylene, polystyrene, polyurethane, polyamide, epoxy resins, urea resins, and acrylic powders. Non limiting examples of useful particles are Microease 110S, 114S, 116 (micronized synthetic waxes), Micropoly 210, 250S (micronized polyethylene), Microslip (micronized polytetrafluoroethylene), and Microsilk (combination of polyethylene and polytetrafluoroethylene), all of which are available from Micro Powder, Inc. Other examples include Luna (smooth silica particles) particles available from Phenomenex, MP-2200 (polymethylmethacrylate), EA-209

(ethylene/acrylate copolymer), SP-501(nylon-12), ES-830 (polymethly methacrylate), BPD-800, BPD-500 (polyurethane) particles available from Kobo Products, Inc. and silicone resins sold under the name Tospearl particles by GE Silicones. Ganzpearl GS-0605 crosslinked polystyrene (available from Presperse) is also useful.

Non limiting examples of hybrid particles include Ganzpearl GSC-30SR (Sericite & crosslinked polystyrene hybrid powder), and SM-1000, SM-200 (mica and silica hybrid powder available from Presperse).

In one embodiment of the present invention, the particles used in the shampoo composition are hollow particles. In a preferred embodiment, the hollow particles are fluid-encapsulated, flexible microspheres. The microspheres are structurally hollow, however, they may contain various fluids, which encompass liquids and gases and their isomers. The gases include, but not limited to, butane, pentane, air, nitrogen, oxygen, carbon dioxide, and dimethyl ether. If used, liquids may only partially fill the microspheres. The liquids include water and any compatible solvent. The liquids may also contain vitamins, amino acids, proteins and protein derivatives, herbal extracts, pigments, dyes, antimicrobial agents, chelating agents, UV absorbers, optical brighteners, silicone compounds, perfumes, humectants which are generally water soluble, additional conditioning agents which are generally water insoluble, and mixtures thereof. In one embodiment, water soluble components are preferred encompassed material. In another embodiment, components selected from the group consisting of vitamins, amino acids, proteins, protein derivatives, herbal extracts, and mixtures thereof are preferred encompassed material. In yet another embodiment, components selected from the group consisting of vitamin E, pantothenyl ethyl ether, panthenol, Polygonum multiflori extracts, and mixtures thereof are preferred encompassed material.

The particles of the present invention can have surface charges or their surface can be modified with organic or inorganic materials such as surfactants, polymers, and inorganic materials. Particle complexes are also useful. Non-limiting examples of complexes of gas-encapsulated microspheres are DSPCS-I2™ (silica modified ethylene/methacrylate copolymer microsphere) and SPCAT-I2™ (talc modified ethylene/methacrylate copolymer microsphere). Both of these are available from Kobo Products, Inc.

The surface of the particle may be charged through a static development or with the attachment of various ionic groups directly or linked via short, long or branched alkyl groups. The surface charge can be anionic, cationic, zwitterionic or amphoteric in nature.

The wall of the particles of the present invention may be formed from a thermoplastic material. The thermoplastic material may be a polymer or copolymer of at least one monomer selected from the following groups: acrylates, methacrylates, styrene, substituted styrene, unsaturated dihalides, acrylonitriles, methacrylonitrile. The thermoplastic materials may contain amide, ester, urethane, urea, ether, carbonate, acetal, sulfide, phosphate, phosphonate ester, and siloxane linkages. The hollow particles may comprise from 1% to 60% of recurring structural units derived from vinylidene chloride, from 20% to 90% of recurring structural units derived from acrylonitrile and from 1% to 50% of recurring structural units derived from a (meth)acrylic monomer, the sum of the percentages (by weight) being equal to 100. The (meth)acrylic monomer is, for example, a methyl acrylate or methacrylate, and especially the methacrylate. Preferably, the particles are comprised of a polymer or copolymer of at least one monomer selected from expanded or non-expanded vinylidene chloride, acrylic, styrene, and (meth)acrylonitrile. More preferably, the particles are comprised of a copolymer of acrylonitrile and methacrylonitrile.

Particles comprised of polymers and copolymers obtained from esters, such as, for example, vinyl acetate or lactate, or acids, such as, for example, itaconic, citraconic, maleic or fumaric acids may also be used. See, in this regard, Japanese Patent Application No. JP-A-2-112304, the full disclosure of which is incorporated herein by reference.

Non-limiting examples of commercially available suitable particles are 551 DE (particle size range of approximately 30–50 $\mu$m and density of approximately 42 kg/m$^3$), 551 DE 20 (particle size range of approximately 15–25 $\mu$m and density of approximately 60 kg/m$^3$), 461 DE (particle size range of approximately 20–40 $\mu$m and density 60 kg/r$^3$), 551 DE 80 (particle size of approximately 50–80 $\mu$m and density of approximately 42 kg/M$^3$), 091 DE (particle size range of approximately 35–55 $\mu$m and density of approximately 30 kg/M$^3$), all of which are marketed under the trademark EXPANCEL™ by Akzo Nobel. Other examples of suitable particles for use herein are marketed under the trademarks DUALITE® and MICROPEARL™ series of microspheres from Pierce & Stevens Corporation. Particularly preferred hollow particles are 091 DE and 551DE 50. The hollow particles of the present invention exist in either dry or hydrated state. The aforesaid particles are nontoxic and non irritating to the skin.

Hollow particles that are useful in the invention can be prepared, for example, via the processes described in EP-56,219, EP-348,372, EP-486,080, EP-320,473, EP-112,807 and U.S. Pat. No. 3,615,972, the full disclosure of each of which is incorporated herein by reference.

Alternatively, the wall of the hollow particles useful in the present invention may be formed from an inorganic material. The inorganic material may be a silica, a soda-lime-borosilicate glass, a silica-alumina ceramic, or an alkali alumino silicate ceramic. Non-limiting examples of commercially available suitable low density, inorganic particles are H50/10,000 EPX (particle size range approximately 20–60 $\mu$m), S38 (particle size range approximately 15–65 $\mu$m), W-210 (particle size range approximately 1–12 $\mu$m), W-410 (particle size range approximately 1–24 $\mu$m), W-610 (particle size range approximately 1–40 $\mu$m), G-200 (particle size range approximately 1–12 $\mu$m), G-400 (particle size range approximately 1–24 $\mu$m), G-600 (particle size range approximately 1–40 $\mu$m), all of which are marketed under the trademarks 3M™ Scotchlite™ Glass Bubbles, 3M™ Zeeospheres™ ceramic microspheres, and 3M™ Z-Light Spheres™ Ceramic Microspheres. Also useful are Silica shells (average particle size 3 $\mu$m) available from KOBO Products and LUXSL™ (3–13 $\mu$m mean diameter) available from PQ Corporation.

Preferably, the wall of the hollow particles useful in the invention are flexible. "Flexible", as used herein, means that the hollow particles are easy to compress. When pressure is reduced the hollow paticles regain their original volume. The flexible hollow particles could alter their shape under an applied stress, or thermal expansion and contraction due to temperature change. Thus, the particles could expand upon heating.

The particles of the invention may be permeable or non-permeable. "Permeable", as used herein, means that they permit a liquid or gas to pass through them under given conditions. Preferably, a majority of the particles of the present invention will maintain their structural integrity during normal use of the shampoo composition. More preferably, substantially all of the particles maintain their structural integrity during normal use of the shampoo composition.

Prefered particles will also have physical properties which are not significantly affected by typical processing of the composition. Preferably, particles having melting points greater than about 70° C. are used. Still more preferably, particles having a melting point greater than 80° C. are used and most preferrably particles having melting point of greater than about 95° C. are used. As used herein, melting point would refer to the temperature at which the particle transitions to a liquid or fluid state or undergoes significant deformation or physical property changes. In addition, many of the particles of present invention are cross-linked or have a cross-linked surface membrane. These particles do not exhibit a distinct melting point. Cross-linked particles are also useful as long as they are stable under the processing and storage conditions used in the making of the present compositions.

Conditioning Agents

Conditioning agents include any material which is used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The conditioning agents useful in the shampoo compositions of the present invention typically comprise a water insoluble, water dispersible, non-volatile, liquid that forms emulsified, liquid particles or are solubilized by the surfactant micelles, in the anionic detersive surfactant component (described above). Suitable conditioning agents for use in the shampoo composition are those conditioning agents characterized generally as silicones (e.g. silicone oils, cationic silicones, silicone gums, high refractive silicones, and silicone resins), organic conditioning oils (e.g. hydrocarbon oils, polyolefins, and fatty esters) or combinations thereof, or those conditioning agents which otherwise form liquid, dispersed, particles in the aqueous surfactant matrix herein. Such conditioning agents should be physically and chemically compatible with the essential components of the composition, and should not otherwise unduly impair product stability, aesthetics or performance.

The concentration of the conditioning agent in the shampoo composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

1. Silicones

The conditioning agent of the shampoo compositions of the present invention is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair (especially when high refractive index (e.g. above about 1.46) silicone conditioning agents are used (e.g. highly phenylated silicones).

The concentration of the silicone conditioning agent typically ranges from about 0.01% to about 10%, by weight of the composition, preferably from about 0.1% to about 8%, more preferably from about 0.1% to about 5%, most preferably from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609, which descriptions are incorporated herein by reference. The silicone conditioning agents for use in the shampoo compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, most preferably from about 100,000 to about 1,500,000 csk.

The dispersed, silicone conditioning agent particles typically have a number average particle diameter ranging from about 0.01 μm to about 50 μm. For small particle application to hair, the number average particle diameters typically range from about 0.01 μm to about 4 μm, preferably from about 0.01 μm to about 2 μm, more preferably from about 0.01 μm to about 0.5 μm. For larger particle application to hair, the number average particle diameters typically range from about 4 μm to about 50 μm, preferably from about 6 μm to about 30 μm, more preferably from about 9 μm to about 20 μm, most preferably from about 12 μm to about 18 μm. Conditioning agents having an average particle size of less than about 5 μm may deposit more efficiently on the hair. It is believed that small size particles of conditioning agent are contained within the coacervate that is formed between the anionic surfactant component (described above) and the cationic polymer component (described below), upon dilution of the shampoo.

Background material on silicones including sections discussing silicone fluids, gums, and resins, as well as manufacture of silicones, are found in *Encyclopedia of Polymer Science and Engineering*, vol. 15, 2d ed., pp 204–308, John Wiley & Sons, Inc. (1989), incorporated herein by reference.

a. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 10 csk to about 100,000 csk. Suitable silicone oils for use in the shampoo compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (III):

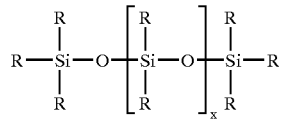

wherein R is aliphatic, preferably alkyl or alkenyl, or aryl, R can be substituted or unsubstituted, and x is an integer from 1 to about 8,000. Suitable unsubstituted R groups for use in the shampoo compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions herein, and are capable of being deposited on and conditioning the hair. The two R groups on the silicon atom of each monomeric silicone unit may represent the same or different groups. Preferably, the two R groups represent the same group.

Preferred alkyl and alkenyl substituents are $C_1$ to $C_5$ alkyls and alkenyls, more preferably from $C_1$ to $C_4$, most preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, most preferably from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is preferably as described above. The R substituents may also be substituted with other groups, such as halogens (e.g. chloride, fluoride, and bromide), halogenated aliphatic or aryl groups, hydroxy (e.g. hydroxy substituted aliphatic groups), and mixtures thereof. Suitable halogenated R groups could include, for example, tri-halogenated (preferably tri-fluoro) alkyl groups such as —$R^1CF_3$, wherein $R^1$ is a $C_1$–$C_3$ alkyl. An example of such a polysiloxane includes, but is not limited to, polymethyl 3,3,3-trifluoropropylsiloxane.

Suitable R groups for use in the shampoo compositions of the present invention include, but are not limited to: methyl, ethyl, propyl, phenyl, methylphenyl and phenylmethyl. Specific non-limiting examples of preferred silicones include: polydimethyl siloxane, polydiethylsiloxane, and polymethylphenylsiloxane. Polydimethylsiloxane is especially preferred. Other suitable R groups include: methyl, methoxy, ethoxy, propoxy, and aryloxy. The three R groups on the end caps of the silicone may represent the same or different groups.

Non-volatile polyalkylsiloxane fluids that may be used include, for example, low molecular weight polydimethylsiloxanes. These siloxanes are available, for example, from the General Electric Company in their Viscasil R and SF 96 series, and from Dow Corning in their Dow Corning 200 series. Polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid. Polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and the composition described herein.

Alkylamino substituted silicones suitable for use in the shampoo compositions of the present invention include, but are not limited to, those which conform to the following general Formula (IV):

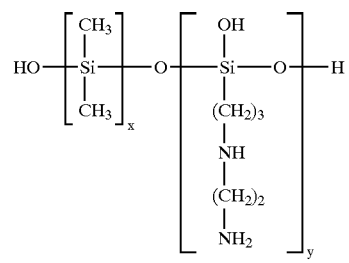

wherein x and y are integers. This polymer is also known as "amodimethicone."

b. Cationic Silicones

Cationic silicone fluids suitable for use in the shampoo compositions of the present invention include, but are not limited to, those which conform to the general formula (V):

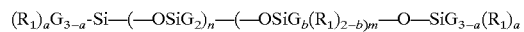

wherein G is hydrogen, phenyl, hydroxy, or $C_1$–$C_8$ alkyl, preferably methyl; a is 0 or an integer having a value from 1 to 3, preferably 0; b is 0 or 1, preferably 1; n is a number from 0 to 1,999, preferably from 49 to 149; m is an integer from 1 to 2,000, preferably from 1 to 10; the sum of n and m is a number from 1 to 2,000, preferably from 50 to 150; $R_1$ is a monovalent radical conforming to the general formula $CqH_{2q}L$, wherein q is an integer having a value from 2 to 8 and L is selected from the following groups:

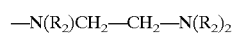

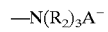

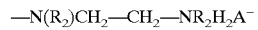

wherein $R_2$ is hydrogen, phenyl, benzyl, or a saturated hydrocarbon radical, preferably an alkyl radical from about $C_1$ to about $C_{20}$, and $A^-$ is a halide ion.

An especially preferred cationic silicone corresponding to formula (V) is the polymer known as "trimethylsilylamodimethicone", which is shown below in formula (VI):

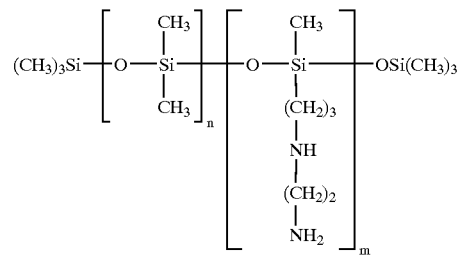

Other silicone cationic polymers which may be used in the shampoo compositions of the present invention are represented by the general formula (VII):

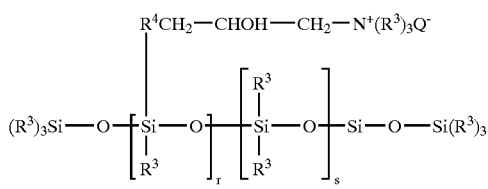

wherein $R^3$ is a monovalent hydrocarbon radical from $C_1$ to $C_{18}$, preferably an alkyl or alkenyl radical, such as methyl; $R_4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; Q is a halide ion, preferably chloride; r is an average statistical value from 2 to 20, preferably from 2 to 8; s is an average statistical value from 20 to 200, preferably from 20 to 50. A preferred polymer of this class is known as UCARE SILICONE ALE 56™, available from Union Carbide.

c. Silicone Gums

Other silicone fluids suitable for use in the shampoo compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76, all of which are incorporated herein by reference. The silicone gums will typically have a weight average molecular weight in excess of about 200,000, preferably from about 200,000 to about 1,000,000. Specific non-limiting examples of silicone gums for use in the shampoo compositions of the present invention include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

d. High Refractive Index Silicones

Other non-volatile, insoluble silicone fluid conditioning agents that are suitable for use in the shampoo compositions of the present invention are those known as "high refractive index silicones," having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

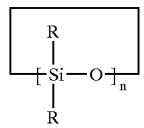

wherein R is as defined above, and n is a number from about 3 to about 7, preferably from about 3 to about 5.

The high refractive index polysiloxane fluids contain an amount of aryl-containing R substituents sufficient to increase the refractive index to the desired level, which is described above. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted. Substituents include aliphatic substituents, and may also include alkoxy substituents, acyl substituents, ketones, halogens (e.g., Cl and Br), amines, and the like. Examples of aryl-containing groups include, but are not limited to, substituted and unsubstituted arenes, such as phenyl, and phenyl derivatives, such as phenyls with $C_1$–$C_5$ alkyl or alkenyl substituents. Specific non-limiting examples include: allylphenyl, methyl phenyl and ethyl phenyl, vinyl phenyls (e.g. styrenyl), and phenyl alkynes (e.g. phenyl $C_2$–$C_4$ alkynes). Heterocyclic aryl groups include, but are not limited to, substituents derived from furan, imidazole, pyrrole, pyridine, and the like. Examples of fused aryl ring substituents include, but are not limited to, napthalene, coumarin, and purine.

Generally, the high refractive index polysiloxane fluids will have a degree of aryl-containing substituents of at least about 15%, preferably at least about 20%, more preferably at least about 25%, even more preferably at least about 35%, most preferably at least about 50%. Typically, the degree of aryl substitution will be less than about 90%, more generally less than about 85%, preferably from about 55% to about 80%.

The high refractive index polysiloxane fluids are also characterized by relatively high surface tensions as a result of their aryl substitution. Generally, the polysiloxane fluids will have a surface tension of at least about 24 dynes/cm$^2$, typically at least about 27 dynes/cm$^2$. Surface tension, for purposes hereof, is measured by a de Nouy ring tensiometer according to Dow Corning Corporate Test Method CTM 0461 23, (Nov. 1971). Changes in surface tension can be measured according to the above test method or according to ASTM Method D 1331.

Preferred high refractive index polysiloxane fluids have a combination of phenyl or phenyl derivative substituents (most preferably phenyl), with alkyl substituents, preferably $C_1$–$C_4$ alkyl (most preferably methyl), hydroxy, or $C_1$–$C_4$ alkylamino (especially —$R^1NHR^2NH2$ wherein each $R^1$ and $R^2$ independently is a $C_1$–$C_3$ alkyl, alkenyl, and/or alkoxy). High refractive index polysiloxanes are available from Dow Corning, Huls America, and General Electric.

When high refractive index silicones are used in the shampoo compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions. Generally, an amount of the spreading agent is used that is sufficient to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture may improve shine of the hair.

Also, the spreading agent will preferably reduce the surface tension by at least about 2 dynes/cm$^2$, preferably at least about 3 dynes/cm$^2$, even more preferably at least about 4 dynes/cm$^2$, most preferably at least about 5 dynes/cm$^2$.

The surface tension of the mixture of the polysiloxane fluid and the spreading agent, at the proportions present in the final product, is preferably less than or equal to about 30 dynes/cm$^2$, more preferably less than or equal to about 28 dynes/cm$^2$, most preferably less than or equal to about 25 dynes/cm$^2$. Typically, the surface tension will be in the range from about 15 dynes/cm$^2$ to about 30 dynes/cm$^2$, more typically from about 18 dynes/cm$^2$ to about 28 dynes/cm$^2$, and most generally from about 20 dynes/cm$^2$ to about 25 dynes/cm$^2$.

The weight ratio of the highly arylated polysiloxane fluid to the spreading agent will, in general, be from about 1000:1 to about 1:1, preferably from about 100:1 to about 2:1, more preferably from about 50:1 to about 2:1, most preferably from about 25:1 to about 2:1. When fluorinated surfactants are used, particularly high polysiloxane fluid to spreading agent ratios may be effective due to the efficiency of these surfactants. Thus, it is contemplated that ratios significantly above 1000:1 may be used.

Silicone fluids suitable for use in the shampoo compositions of the present invention are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984), all of which are incorporated herein by reference.

e. Silicone Resins

Silicone resins may be included in the silicone conditioning agent of the shampoo compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin. As is apparent to one of ordinary skill in the art, the degree of cross-linking that is required in order to result in a silicone resin will vary according to the specific silane units incorporated into the silicone resin. Generally, silicone materials which have a sufficient level of trifunctional and tetrafunctional siloxane monomer units (and hence, a sufficient level of cross-linking) such that they dry down to a rigid, or hard, film are considered to be silicone resins. The ratio of oxygen atoms to silicon atoms is indicative of the level of cross-linking in a particular silicone material. Silicone resins suitable for use in the shampoo compositions of the present invention generally have at least about 1.1 oxygen atoms per silicon atom. Preferably, the ratio of oxygen to silicon atoms is at least about 1.2:1.0. Silanes used in the manufacture of silicone resins include, but are not limited to: monomethyl-, dimethyl-, trimethyl-, monophenyl-, di-phenyl-, methylphenyl-, monovinyl-, and methylvinyl-chlorosilanes, and tetrachlorosilane, with the methyl-substituted silanes being most commonly utilized. Preferred resins are available from General Electric as GE SS4230 and GE SS4267. Commercially available silicone resins are generally supplied in a dissolved form in a low viscosity volatile or non-volatile silicone fluid. The silicone resins for use herein should be supplied and incorporated into the present compositions in such dissolved form, as will be readily apparent to one of ordinary skill in the art.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence. Typical alternate substituents include, but are not limited to, groups such as vinyl, phenyls, amines, hydroxyls, and the like. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin indicates higher levels of cross-linking. As discussed above, however, the overall level of cross-linking can also be indicated by the oxygen to silicon ratio.

Preferred silicone resins for use in the shampoo compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, most preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

2. Organic Conditioning Oils

The conditioning component of the shampoo compositions of the present invention may also comprise from about 0.05% to about 3%, by weight of the composition, preferably from about 0.08% to about 1.5%, more preferably from about 0.1% to about 1%, of at least one organic conditioning oil as the conditioning agent, either alone or in combination with other conditioning agents, such as the silicones (described above).

It is believed that these organic conditioning oils provide the shampoo composition with improved conditioning performance when used in combination with the essential components of the composition, and in particular when used in combination with cationic polymers (described below). The conditioning oils may add shine and luster to the hair. Additionally, they may enhance dry combing and dry hair feel. Most or all of these organic conditioning oils are believed to be solubilized in the surfactant micelles of the shampoo composition. It is also believed that this solubilization into the surfactant micelles contributes to the improved hair conditioning performance of the shampoo compositions herein.

The organic conditioning oils suitable for use as the conditioning agent herein are preferably low viscosity, water insoluble, liquids selected from the hydrocarbon oils, polyolefins, fatty esters, and mixtures thereof. The viscosity, as measured at 40° C., of such organic conditioning oils is preferably from about 1 centipoise to about 200 centipoise, more preferably from about 1 centipoise to about 100 centipoise, most preferably from about 2 centipoise to about 50 centipoise.

a. Hydrocarbon Oils

Suitable organic conditioning oils for use as conditioning agents in the shampoo compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation.

b. Polyolefins

Organic conditioning oils for use in the shampoo compositions of the present invention can also include liquid polyolefins, more preferably liquid poly-α-olefins, most preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

c. Fatty Esters

Other suitable organic conditioning oils for use as the conditioning agent in the shampoo compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Suitable for use in the shampoo compositions of the present invention are alkyl and alkenyl esters of fatty acids having from about $C_{10}$ to about $C_{22}$ aliphatic chains, and alkyl and alkenyl fatty alcohol carboxylic acid esters having a $C_{10}$ to about $C_{22}$ alkyl and/or alkenyl alcohol-derived aliphatic chain, and mixtures thereof. Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the shampoo compositions of the present invention are mono-carboxylic acid esters of the general formula R'COOR, wherein R' and R are alkyl or alkenyl radicals, and the sum of carbon atoms in R' and R is at least 10, preferably at least 20. The mono-carboxylic acid ester need not necessarily contain at least one chain with at least 10 carbon atoms; rather the total number of aliphatic chain carbon atoms must be least 10. Specific non-limiting examples of mono-carboxylic acid esters include: isopropyl myristate, glycol stearate, and isopropyl laurate.

Still other fatty esters suitable for use in the shampoo compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, adipic acid, hexanoic acid, heptanoic acid, and octanoic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the shampoo compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the shampoo compositions of the present invention are glycerides, including, but not limited to, mono-, di-, and tri-glycerides, preferably di- and tri-glycerides, most preferably triglycerides. For use in the shampoo compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the shampoo compositions of the present invention are water insoluble synthetic fatty esters. Some preferred synthetic esters conform to the general Formula (IX):

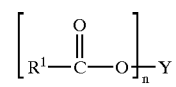

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (X):

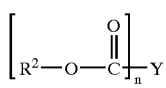

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (X).

It is believed that the preferred synthetic esters provide improved wet hair feel when used in combination with the essential components of the shampoo compositions of the present invention, particularly when used in combination with the cationic polymer component (described below). These synthetic esters improve wet hair feel by reducing the slimy or excessively conditioned feel of wet hair that has been conditioned by a cationic polymer.

Specific non-limiting examples of suitable synthetic fatty esters for use in the shampoo compositions of the present invention include: P-43 ($C_8$–$C_{10}$ triester of trimethylolpropane), MCP-684 (tetraester of 3,3 diethanol-1,5 pentadiol), MCP 121 ($C_8$–$C_{10}$ diester of adipic acid), all of which are available from Mobil Chemical Company.

3. Other Conditioning Agents

Also suitable for use in the compositions herein are the conditioning agents described by the Procter & Gamble Company in U.S. Pat. Nos. 5,674,478, and 5,750,122, both of which are incorporated herein in their entirety by reference. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal), all of which descriptions are incorporated herein by reference.

Some other preferred silicone conditioning agents for use in the compositions of the present invention include: Abil® S 201 (dimethicone/sodium PG-propyldimethicone thiosulfate copolymer), available from Goldschmidt; DC Q2-8220 (trimethylsilyl amodimethicone) available from Dow Corning; DC 949 (amodimethicone, cetrimonium chloride, and Trideceth-12), available from Dow Corning; DC 749 (cyclomethicone and trimethylsiloxysilicate), available from Dow Corning; DC2502 (cetyl dimethicone), available from Dow Corning; BC97/004 and BC 99/088 (amino functionalized silicone microemulsions), available from Basildon Chemicals; GE SME253 and SM2115-D2 and SM2658 and SF1708 (amino functionalized silicone microemulsions), available from General Electric; siliconized meadowfoam seed oil, available from Croda; and those silicone conditioning agents described by GAF Corp. in U.S. Pat. No. 4,834,767 (quaternized amino lactam), by Biosil Technologies in U.S. Pat. No. 5,854,319 (reactive silicone emulsions containing amino acids), and by Dow Corning in U.S. Pat. No. 4,898,585 (polysiloxanes), all of which descriptions are incorporated herein by reference.

Anti-dandruff Actives

The shampoo compositions of the present invention may also contain an anti-dandruff agent. Suitable, non-limiting examples of anti-dandruff particulates include: pyridinethione salts, selenium sulfide, particulate sulfur, and mixtures thereof. Preferred are pyridinethione salts. Such anti-dandruff particulate should be physically and chemically compatible with the essential components of the composition, and should not otherwise unduly impair product stability, aesthetics or performance.

1. Pyridinethione Salts

Pyridinethione anti-dandruff particulates, especially 1-hydroxy-2-pyridinethione salts, are highly preferred particulate anti-dandruff agents for use in shampoo compositions of the present invention. The concentration of pyridinethione anti-dandruff particulate typically ranges from about 0.1% to about 4%, by weight of the composition, preferably from about 0.1% to about 3%, most preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), most preferably 1-hydroxy-2-pyridinethione salts in platelet particle form, wherein the particles have an average size of up to about 20$\mu$, preferably up to about 5, most preferably up to about 2.5$\mu$. Salts formed from other cations, such as sodium, may also be suitable. Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982, all of which are incorporated herein by reference. It is contemplated that when ZPT is used as the anti-dandruff particulate in the shampoo compositions herein, that the growth or re-growth of hair may be stimulated or regulated, or both, or that hair loss may be reduced or inhibited, or that hair may appear thicker or fuller.

2. Selenium Sulfide

Selenium sulfide is a particulate anti-dandruff agent suitable for use in the shampoo compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 $\mu$m, as measured by forward laser light scattering device (e.g. Malvern 3600 instrument), preferably less than 10 $\mu$m. Selenium sulfide compounds are described, for example, in U.S. Pat. No. 2,694,668; U.S. Pat. No. 3,152,046; U.S. Pat. No. 4,089,945; and U.S. Pat. No. 4,885,107, all of which descriptions are incorporated herein by reference.

3. Sulfur

Sulfur may also be used as a particulate anti-dandruff agent in the shampoo compositions of the present invention. Effective concentrations of the particulate sulfur are typically from about 1% to about 4%, by weight of the composition, preferably from about 2% to about 4%.

Humectant

The compositions of the present invention may contain a humectant. The humectants herein are selected from the group consisting of polyhydric alcohols, water soluble alkoxylated nonionic polymers, and mixtures thereof. The humectants, when used herein, are preferably used at levels by weight of the composition of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosarine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

Commercially available humectants herein include: glycerin with tradenames STAR™ and SUPEROL™ available from The Procter & Gamble Company, CRODEROL GA7000™ available from Croda Universal Ltd., PRECERIN™ series available from Unichema, and a same tradename as the chemical name available from NOF; propylene glycol with tradename LEXOL PG-865/855™ available from Inolex, 1,2-PROPYLENE GLYCOL USP available from BASF; sorbitol with tradenames LIPONIC™ series available from Lipo, SORBO™, ALEX™, A-625™, and A-641™ available from ICI, and UNISWEET 70™, UNISWEET CONC™ available from UPI; dipropylene glycol with the same tradename available from BASF; diglycerin with tradename DIGLYCEROL™ available from Solvay GmbH; xylitol with the same tradename available from Kyowa and Eizai; maltitol with tradename MALBIT available from Hayashibara, sodium chondroitin sulfate with the same tradename available from Freeman and Bioiberica, and with tradename ATOMERGIC SODIUM CHONDROITIN SULFATE available from Atomergic Chemetals; sodium hyaluronate with tradenames ACTIMOIST available from Active Organics, AVIAN SODIUM HYALURONATE series available from Intergen, HYALURONIC ACID Na available from Ichimaru Pharcos; sodium adenosine phosphate with the same tradename available from Asahikasei, Kyowa, and Daiichi Seiyaku; sodium lactate with the same tradename available from Merck, Wako, and Showa Kako, cyclodextrin with tradenames CAVITRON available from American Maize, RHODOCAP series available from Rhone-Poulenc, and DEXPEARL available from Tomen; and polyethylene glycols with the tradename CARBOWAX series available from Union Carbide.

Suspending Agent

The shampoo compositions of the present invention may further comprise a suspending agent at concentrations effective for suspending the particle, or other water-insoluble material, in dispersed form in the shampoo compositions or for modifying the viscosity of the composition. Such concentrations range from about 0.1% to about 10%, preferably from about 0.3% to about 5.0%, by weight of the shampoo compositions.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyalkylene glycols having a molecular weight of more than about 1000, polyacrylamide, polyethyleneimine, and inorganic water soluble material such as bentonite, aluminum magnesium silicate, laponite, hectonite, and anhydrous silicic acid.

Other Optional Components

The compositions of the present invention may contain also vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names: Acid Red 18, 26, 27,33, 51, 52, 87, 88, 92, 94, 95, Acid Yellow 1, 3, 11, 23, 36, 40, 73, Food Yellow 3, Food Green 3, Food blue 2, Food Red 1, 6, Acid Blue 5, 9, 74, Pigment Red 57-1, 53(Na), Basic Violet 10, Solvent Red 49, Acid orange 7, 20, 24, Acid Green 1, 3, 5, 25, Solvent Green 7, Acid Violet 9, 43; water insoluble components such as those having C. I. Names: Pigment Red 53(Ba), 49(Na), 49(Ca), 49(Ba), 49(Sr), 57, Solvent Red 23, 24, 43, 48, 72, 73, Solvent Orange 2, 7, Pigment Red 4, 24, 48, 63(Ca)3, 64, Vat Red 1, Vat blue 1, 6, Pigment Orange 1, 5, 13, Solvent Yellow 5, 6, 33, Pigment Yellow 1, 12, Solvent Green 3, Solvent Violet 13, Solvent Blue 63, Pigment Blue 15, titanium dioxides, chlorophyllin copper complex, ultramarines, aluminum powder, bentonite, calcium carbonate, barium sulfate, bismuthine, calcium sulfate, carbon black, bone black, chromic acid, cobalt blue, gold, ferric oxides, hydrated ferric oxide, ferric ferrocyanide, magnesium carbonate, manganous phosphate, silver, and zinc oxides.

The compositions of the present invention may also contain antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

The compositions of the present invention may also contain chelating agents such as: 2,2'-dipyridylamine; 1,10-phenanthroline {o-phenanthroline}; di-2-pyridyl ketone; 2,3-bis(2-pyridyl)pyrazine; 2,3-bis(2-pyridyl)-5,6-dihydropyrazine; 1,1'-carbonyldiimidazole; 2,4-bis(5,6-diphenyl-1,2,4-triazine-3-yl)pyridine; 2,4,6-tri(2-pyridyl)-1,3,5-triazine; 4,4'-dimethyl-2,2'dipyridyl; 2,2'-biquinoline; di-2-pyridyl glyoxal {2,2'-pyridil}; 2-(2-pyridyl) benzimidazole; 2,2'-bipyrazine; 3-(2-pyridyl)-5,6-diphenyl-1,2,4-trazine; 3-(4-phenyl-2-pyridyl)-5-phenyl-1,2,4-triazine; 3-(4-phenyl-2-pyridyl)-5,6-diphenyl-1,2,4-triazine; 2,3,5,6-tetrakis-(2'-pyridyl)-pyrazine; 2,6-pyridinedicarboxylic acid; 2,4,5-trihydroxypyrimidine; phenyl 2-pyridyl ketoxime; 3-amino-5,6-dimethyl-1,2,4-triazine; 6-hydroxy-2-phenyl-3(2H)-pyridazinone; 2,4-pteridinediol {lumazine}; 2,2'-dipyridyl; and 2,3-dihydroxypyridine.

Method of Use

The shampoo compositions of the present invention are used in a conventional manner for cleansing hair or skin and providing enhanced deposition of solid particles and other benefits of the present invention. An effective amount of the composition for cleansing the hair or skin is applied to the hair or skin, that has preferably been wetted with water, and then rinsed off. Such effective amounts generally range from about 1 g to about 50 g, preferably from about 1 g to about 20 g. Application to the hair typically includes working the composition through the hair such that most or all of the hair is contacted with the composition.

This method for cleansing the hair and skin comprises the steps of:

a) wetting the hair and/or skin with water, b) applying an effective amount of the shampoo composition to the hair and/or skin, and c) rinsing the composition from the hair and/or skin using water. These steps can be repeated as many times as desired to achieve the desired cleansing and particle deposition benefits.

The following examples further describe and demonstrate the preferred embodiments within the scope of the present invention. The examples are given solely for the purpose of illustration, and are not to be construed as limitations of the present invention since many variations thereof are possible without departing from its scope.

EXAMPLES

The shampoo compositions illustrated in the following Examples illustrate specific embodiments of the shampoo compositions of the present invention, but are not intended to be limiting thereof. Other modifications can be undertaken by the skilled artisan without departing from the spirit and scope of this invention. These exemplified embodiments of the shampoo composition of the present invention provide enhanced deposition efficiency benefits of the particles.

The shampoo compositions illustrated in the following Examples are prepared by conventional formulation and mixing methods, an example of which is set forth hereinbelow. All exemplified amounts are listed as weight percents and exclude minor materials such as diluents, preservatives, color solutions, imagery ingredients, botanicals, and so forth, unless otherwise specified.

The shampoo compositions of the present invention may be prepared using conventional formulation and mixing techniques. Where melting or dissolution of solid surfactants or wax components is required these can be added to a premix of the surfactants, or some portion of the surfactants, mixed and heated to melt the solid components, e.g., about 72° C. This mixture can then optionally be processed through a high shear mill and cooled, and then the remaining components are mixed in. The solid particle component can be added either prior to processing through a high shear mill or preferably added to this final mix, after cooling. The compositions typically have a final viscosity of from about 2000 to about 20,000 cps. The viscosity of the composition can be adjusted by conventional techniques including addition of sodium chloride or ammonium xylenesulfonate as needed. The listed formulations, therefore, comprise the listed components and any minor materials associated with such components.

|  | Example 1 | Example 2 | Example 3 | Example 4 |
|---|---|---|---|---|
| Ammonium Laureth Sulfate | 10.00 | 10.00 | 10.00 |  |
| Ammonium Lauryl Sulfate | 6.00 | 6.00 | 4.00 |  |
| Sodium Laureth Sulfate |  |  |  | 10.00 |
| Sodium Lauryl Sulfate |  |  |  | 6.00 |
| Cocamidopropyl Betaine |  |  | 2.00 |  |
| Ethylene Glycol Distearate | 1.50 | 1.50 | 1.50 | 1.50 |
| CMEA | 0.800 | 0.800 | 0.800 | 0.800 |
| Cetyl Alcohol | 0.900 | 0.900 | 0.900 | 0.900 |
| Guar Hydroxypropyl trimonium chloride (1) | 0.500 | 0.500 | 0.650 | 0.500 |
| Dimethicone (2) | 2.35 | 2.35 | 2.35 | 1.25 |
| Trimethylolpropane tricaprylate/tricaprate (3) | 0.100 | 0.100 | 0.100 | 0.100 |
| Hydrogenated Polydecene (4) | 0.400 | 0.400 | 0.400 | 0.400 |
| ZPT (5) |  | 1.00 | 1.00 | 1.00 |
| Sodium Citrate | 0.400 | 0.400 | 0.400 | 0.200 |
| Citric Acid | 0.0400 | 0.0400 | 0.0400 | 0.2200 |
| Sodium Chloride | 1.475 | 1.475 | 1.475 | 1.475 |
| Perfume | 0.700 | 0.700 | 0.700 | 0.700 |
| Sodium Benzoate | 0.250 | 0.250 | 0.250 | 0.250 |
| Kathon | 0.0005 | 0.0005 | 0.0005 | 0.0005 |
| Benzyl Alcohol | 0 | 0 | 0 | 0 |
| Water | q.s. | q.s. | q.s. | q.s. |

(1) Guar having a molecular weight of about 400,000, and having a charge density of about 2.10 meq/g, available from Aqualon.
(2) Viscasil 330M available from General Electric Silicones
(3) Mobil P43, available from Mobil.
(4) Puresyn 6, available from Mobil.
(5) ZPT having an average particle size of about 2.5 mm, available from Arch/Olin.

|  | Example 5 | Example 6 | Example 7 | Example 8 | Example 9 |
|---|---|---|---|---|---|
| Ammonium Laureth Sulfate | 10.00 | 10.00 | 10.00 | 7.00 |  |
| Ammonium Lauryl Sulfate | 6.00 | 6.00 | 2.00 | 6.50 |  |
| Sodium Laureth Sulfate |  |  |  |  | 10.00 |
| Sodium Lauryl Sulfate |  |  |  |  | 6.00 |
| Sodium Lauroamphoacetate |  |  | 4.00 |  |  |
| Ethylene Glycol Distearate | 1.50 | 1.50 | 1.50 | 1.50 | 1.50 |
| CMEA | 0.800 | 0.800 | 0.800 | 0.800 | 0.800 |
| Cetyl Alcohol | 0.900 | 0.900 | 0.900 | 0.900 | 0.900 |

-continued

|  | Example 5 | Example 6 | Example 7 | Example 8 | Example 9 |
|---|---|---|---|---|---|
| Guar Hydroxypropyl trimonium chloride (6) | 0.500 |  | 0.350 |  |  |
| Guar Hydroxypropyl trimonium chloride (7) |  | 0.500 |  | 0.500 | 0.500 |
| Dimethicone (8) | 2.35 | 2.35 | 2.35 | 2.35 | 2.35 |
| Trimethylolpropane tricaprylate/tricaprate (9) | 0.100 | 0.100 | 0.100 | 0.100 | 0.100 |
| Hydrogenated Polydecene (10) | 0.000 | 0.400 | 0.400 | 0.400 | 0.400 |
| ZPT (11) |  |  | 1.00 | 1.00 | 1.00 |
| Sodium Citrate | 0.400 | 0.400 | 0.400 | 0.400 | 0.200 |
| Citric Acid | 0.0400 | 0.0400 | 0.0400 | 0.0400 | 0.2200 |
| Sodium Chloride | 1.475 | 1.475 | 1.475 | 1.475 | 1.475 |
| Perfume | 0.700 | 0.700 | 0.700 | 0.700 | 0.700 |
| Sodium Benzoate | 0.250 | 0.250 | 0.250 | 0.250 | 0.250 |
| Kathon | 0.0005 | 0.0005 | 0.0005 | 0.0005 | 0.0005 |
| Benzyl Alcohol | 0 | 0 | 0 | 0 | 0 |
| Water | q.s. | q.s. | q.s. | q.s. | q.s. |

(6) Guar having a molecular weight of about 1,100,000, and having a charge density of about 2.10 meq/g, available from Aqualon.
(7) Guar having a molecular weight of about 400,000, and having a charge density of about 1.57 meq/g, available from Aqualon.
(8) Viscasil 330 M available from General Electric Silicones
(9) Mobil P43, available from Mobil.
(10) Puresyn 6, available from Mobil.
(11) ZPT having an average particle size of about 2.5 mm, available from Arch/Olin.

It is understood that the examples and embodiments described herein are for illustrative purposes only and that various modifications or changes in light thereof will be suggested to one skilled in the art without departing from the scope of the present invention.

What is claimed is:

1. A shampoo composition comprising:
   a) from about 5 to about 50 weight percent of a detersive surfactant,
   b) at least about 0.05 weight percent of a cationic guar derivative;
      i) wherein said cationic guar derivative has a molecular weight from about 10,000 to about 10,000,000; and
      ii) wherein said cationic guar derivative has a charge density from about 1.5 meq/g to about 7 meq/g;
   c) at least about 0.1 weight percent of particles having a mean particle size of less than about 300 microns, wherein said particles are selected from the group consisting of hollow particles, solid particles and combinations thereof; and
   d) at least about 20.0 weight percent of an aqueous carrier.

2. The composition of claim 1 wherein said cationic guar derivative has a molecular weight of from about 100,000 to about 3,000,000.

3. The composition of claim 1 wherein said cationic guar derivative has a charge density of from about 1.5 meq/gm to about 5 meq/gm.

4. The composition of claim 1 wherein said cationic guar derivative has a charge density of from about 1.7 meq/gm to about 5 meq/gm.

5. The composition of claim 1 wherein said cationic guar derivative has a charge density of from about 2.0 meq/gm to about 4.5 meq/gm.

6. The composition of claim 1 comprising from about 0.075 weight percent to about 2 weight percent of said cationic guar derivative.

7. The composition of claim 1 wherein the weight ratio of said cationic guar derivative to said particles is from about 1:2 to about 1:10.

8. A composition according to claim 1 further comprising a conditioning agent selected from the group consisting of silicone oils, cationic silicones, silicone gums, high refractive index silicones, silicone resins, hydrocarbon oils, polyolefins, fatty esters and mixtures thereof.

* * * * *